(12) United States Patent
Yamaji et al.

(10) Patent No.: US 10,098,555 B2
(45) Date of Patent: Oct. 16, 2018

(54) BIOLOGICAL INFORMATION MEASUREMENT APPARATUS

(71) Applicant: Murata Manufacturing Co., Ltd., Nagaokakyo-shi, Kyoto-fu (JP)

(72) Inventors: Kazuhiro Yamaji, Nagaokakyo (JP); Hirofumi Tsuchimoto, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 293 days.

(21) Appl. No.: 15/054,311

(22) Filed: Feb. 26, 2016

(65) Prior Publication Data

US 2016/0166162 A1 Jun. 16, 2016

Related U.S. Application Data

(63) Continuation of application No. PCT/JP2014/072225, filed on Aug. 26, 2014.

(30) Foreign Application Priority Data

Aug. 29, 2013 (JP) .................... 2013-178540

(51) Int. Cl.
*A61B 5/02* (2006.01)
*A61B 5/024* (2006.01)
*A61B 5/00* (2006.01)

(52) U.S. Cl.
CPC ........ *A61B 5/02427* (2013.01); *A61B 5/6826* (2013.01)

(58) Field of Classification Search
CPC .......................... A61B 5/02427; A61B 5/6826
See application file for complete search history.

(56) References Cited

U.S. PATENT DOCUMENTS 6,699,199 B2 * 3/2004 Asada ............... A61B 5/14552
600/481
2009/0306487 A1 * 12/2009 Crowe .............. A61B 5/02433
600/322

(Continued)

FOREIGN PATENT DOCUMENTS

JP H0450009 Y2 11/1992
JP 2000083914 A 3/2000

(Continued)

OTHER PUBLICATIONS

International Search Report issued for PCT/JP2014/072225, dated Sep. 22, 2014.

(Continued)

*Primary Examiner* — Michael Carey
*Assistant Examiner* — Natasha Patel
(74) *Attorney, Agent, or Firm* — Arent Fox LLP

(57) ABSTRACT

A biological information measurement apparatus capable of improving the SN ratio of a photoplethysmographic signal by reducing stray light in detection light that reaches a light-receiving unit from a light-emitting unit is provided. A biological information measurement apparatus includes a light-emitting unit that irradiates a finger, a light-receiving unit that receives and photoelectrically converts light transmitted through or reflected by the finger and outputs a photoplethysmographic signal, and a processing unit that obtains biological information on the basis of the photoplethysmographic signal. The light-emitting and light-receiving units are disposed, in plan view in a plane perpendicular to the direction of the emitted light or the received light, such that a line passing through the centers of the light-emitting unit and the light-receiving unit is slanted relative to a lengthwise direction of the finger.

18 Claims, 7 Drawing Sheets

(56) References Cited

U.S. PATENT DOCUMENTS

2014/0058217 A1* 2/2014 Giovangrandi ...... A61B 5/0295
600/301
2015/0190079 A1 7/2015 Yamaji et al.

FOREIGN PATENT DOCUMENTS

| JP | 2012165851 A | 9/2012 |
| JP | 2013000540 A | 1/2013 |
| WO | WO 2014045774 A1 | 3/2014 |

OTHER PUBLICATIONS

Written Opinion of the International Searching Authority issued for PCT/JP2014/072225, dated Sep. 22, 2014.

* cited by examiner

BIOLOGICAL INFORMATION MEASUREMENT APPARATUS

CROSS-REFERENCE TO RELATED APPLICATIONS

The present application is a continuation of PCT/JP2014/072225 filed Aug. 26, 2014, which claims priority to Japanese Patent Application No. 2013-178540, filed Aug. 29, 2013, the entire contents of each of which are incorporated herein by reference.

TECHNICAL FIELD

The present invention relates to biological information measurement apparatuses.

BACKGROUND

Patent Document 1 discloses a biological information measurement apparatus including a detection means including a light-emitting unit that emits light toward part of a biological body and a light-receiving unit that receives the light emitted from the light-emitting unit through the biological body, and a biological information display means that displays biological information on the basis of a detection result from the detection means. According to this biological information measurement apparatus, the detection means is configured such that the light-emitting unit and the light-receiving unit are parallel to a lengthwise direction of a subject's finger, a pulse wave signal is generated from light reflected by hemoglobin in the blood of the subject's finger and received by the light-receiving unit, and the biological information is obtained on the basis of the pulse wave signal.

Patent Document 2 discloses a pulse wave measurement apparatus in which a light-emitting element of a pulse wave sensor is configured to emit light toward a measurement area and extinguish the light in a periodic manner. This pulse wave measurement apparatus includes a light-emitting means that is repeatedly lit and extinguished, a light-receiving means that receives light reflected by or transmitted through the measurement area, and a pulse wave signal generating means that outputs a difference between a light reception signal during a lit period and a light reception signal during an extinguished period as the pulse wave signal. The pulse wave signal generating means includes a first sample holding means that samples and holds the light reception signal during the lit period and a second sample holding means that samples and holds the light reception signal during the extinguished period, and the stated pulse wave signal is outputted on the basis of a difference between the outputs of the two sample holding means.

Patent Document 1: Japanese Unexamined Patent Application Publication No. 2000-83914.

Patent Document 2: Japanese Unexamined Patent Application Publication No. 2012-165851.

Improving SN ratios in pulse wave signal processing is an issue in biological information measurement apparatuses such as that disclosed in Patent Document 1. The biological information is obtained from a pulse wave component in the amplitude of detection light, and thus with detection light constituted of an AC component and a DC component, the AC is a component needed to obtain biological information such as a pulse wave signal, whereas the DC component is an unnecessary component. A higher ratio of the AC component to the total of the AC component and the DC component in the pulse wave signal, or in other words, a higher SN ratio, is therefore preferable for obtaining highly-accurate biological information. A configuration that improves the SN ratio of the pulse wave signal by controlling the light emission timing of the light-emitting means and the processing of the light reception signals, as per the pulse wave measurement apparatus disclosed in Patent Document 2, is problematic because the configuration complicates a control means and thus increases the cost of the apparatus. It is thus desirable to improve the SN ratio of the pulse wave signal by directly reducing the DC component of the detection light.

SUMMARY OF THE INVENTION

Having been achieved in light of the aforementioned problems, it is an object of the present invention to provide a biological information measurement apparatus capable of improving the SN ratio of a photoplethysmographic signal by reducing stray light corresponding to a DC component of detection light that reaches a light-receiving unit from a light-emitting unit.

A biological information measurement apparatus according to the present invention includes a light-emitting unit that irradiates a measurement area, a light-receiving unit that receives and photoelectrically converts light transmitted through or reflected by the measurement area and outputs a photoplethysmographic signal, and a processing unit that obtains biological information on the basis of the photoplethysmographic signal. In an exemplary embodiment, the light-emitting unit and the light-receiving unit are disposed, in plan view in a plane perpendicular to a direction in which the light-emitting unit emits light or a direction in which the light-receiving unit receives light, such that a line passing through the center of the light-emitting unit and the center of the light-receiving unit is slanted relative to a lengthwise direction of the measurement area.

In the biological information measurement apparatus according to the present invention, the light-emitting unit and the light-receiving unit are disposed such that the line connecting the light-emitting unit and the light-receiving unit is slanted relative to the lengthwise direction of the measurement area. Stray light is reduced as a result, and compared to a case where the line that connects the light-emitting unit and the light-receiving unit is parallel to the lengthwise direction of the measurement area, the ratio in which a DC component of detection light decreases relative to the ratio in which an AC component of the detection light decreases is increased. The SN ratio of the photoplethysmographic signal can be improved as a result.

The biological information measurement apparatus according to the present invention further includes a substrate in which the light-emitting unit and the light-receiving unit are formed, and a main body including a guiding means for regulating a position of the measurement area relative to the substrate.

According to this configuration, the measurement area is regulated relative to the substrate in which the light-emitting unit and the light-receiving unit are formed, and as a result, the lengthwise direction of the measurement area can be set to be slanted relative to the line that connects the light-emitting unit and the light-receiving unit with certainty.

Here, the measurement area is a finger; and the guiding means is a cover having a cylindrical hollow cavity portion capable of containing the finger, and is configured such that the line passing through the center of the light-emitting unit and the center of the light-receiving unit is slanted relative to a center axis of the cylindrical hollow cavity portion.

According to this configuration, the finger, which serves as the measurement area, is positioned relative to the light-emitting unit and the light-receiving unit by being held within the hollow cavity portion, and a slant or diagonal can be provided between the lengthwise direction of the finger and the line connecting the light-emitting unit and the light-receiving unit through a simple configuration even in light of varying sizes, varying insertion states, and so on of the finger serving as the measurement area.

Meanwhile, it is preferable that the substrate be configured as a rectangular substrate, the light-emitting unit and the light-receiving unit be disposed at diagonally opposing corner areas of the rectangular substrate, and one pair of sides of the rectangular substrate be parallel to the center axis of the cylindrical hollow cavity portion.

According to this configuration, a slant or diagonal can be provided between the lengthwise direction of the finger and the line connecting the light-emitting unit and the light-receiving unit through a simple configuration through the arrangement of the light-emitting unit and the light-receiving unit on the substrate. Accordingly, there are no additional components to the conventional apparatus, avoiding an increase in apparatus costs.

The biological information measurement apparatus according to the present invention further includes a substrate in which the light-emitting unit and the light-receiving unit are formed, and a main body for defining a position of the substrate relative to the measurement area.

According to this configuration, the substrate in which the light-emitting unit and the light-receiving unit are formed is positioned relative to the measurement area, and thus the line that connects the light-emitting unit and the light-receiving unit can be slanted relative to the lengthwise direction of the measurement area with certainty.

Here, the measurement area is a finger; and the substrate is configured as a rectangular substrate, the light-emitting unit and the light-receiving unit are disposed parallel to a pair of sides of the rectangular substrate, and the rectangular substrate is disposed on the main body such that the pair of sides is slanted relative to the lengthwise direction.

According to this configuration, the lengthwise direction of the finger can be slanted relative to the line that connects the light-emitting unit and the light-receiving unit simply by changing the arrangement of the substrate on the main body, without changing the configuration of the conventional substrate. As such, the process for manufacturing the conventional substrate need not be changed, which suppresses development costs.

In the biological information measurement apparatus according to the present invention, the substrate may be disposed relative to the main body such that an angle formed between the lengthwise direction of the measurement area and the line passing through the center of the light-emitting unit and the center of the light-receiving unit is variable.

According to this configuration, it is possible to specify or adjust the optimum angle between the lengthwise direction of the measurement area and the line connecting the light-emitting unit and the light-receiving unit for obtaining a desired SN ratio in the photoplethysmographic signal.

According to the present invention, in a biological information measurement apparatus that obtains biological information from light transmitted through or reflected by a measurement area after the measurement area is irradiated with light, stray light reaching a light-receiving unit from a light-emitting unit can be reduced and the SN ratio of a photoplethysmographic signal can be improved.

DETAILED DESCRIPTION

Figure 1:
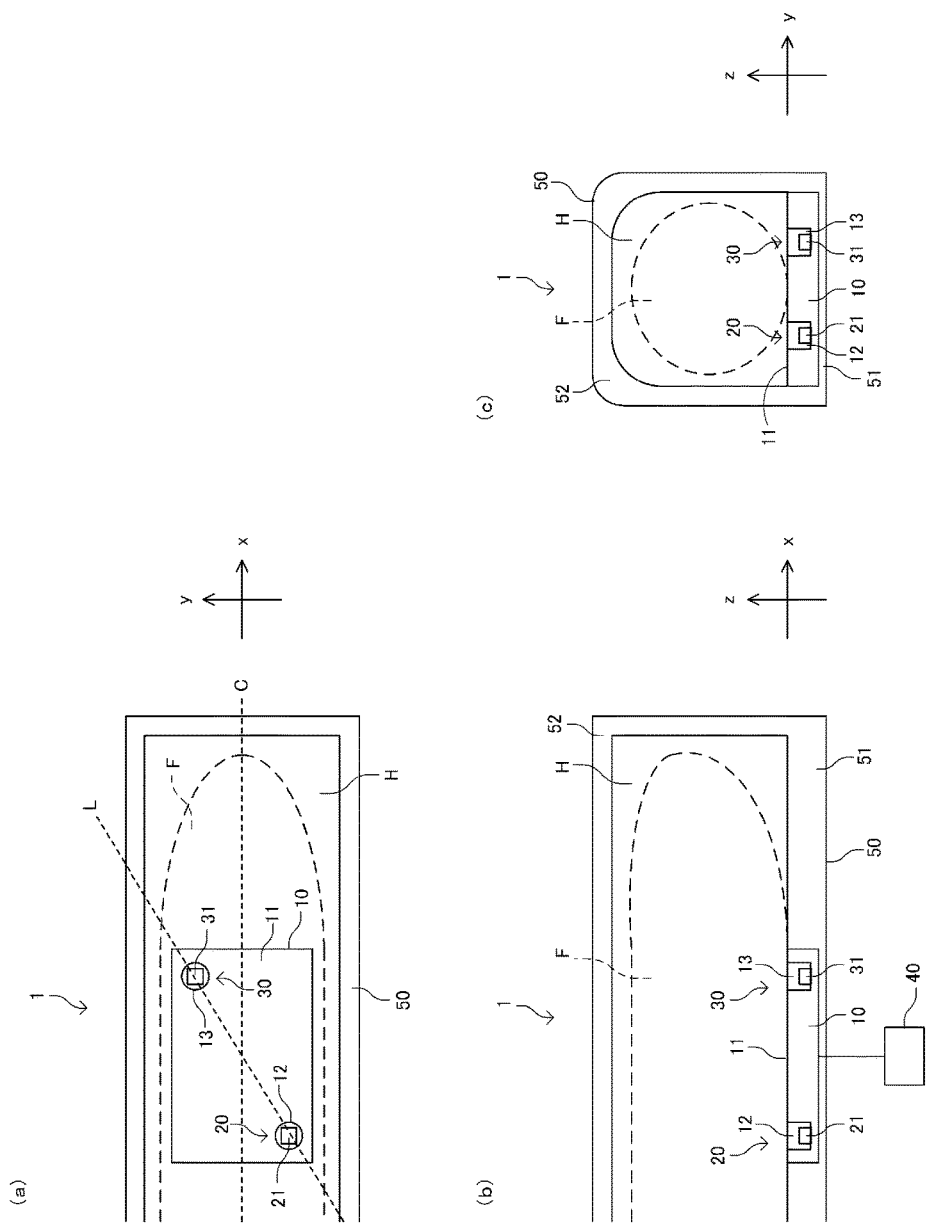
FIG. 1 is a diagram illustrating a biological information measurement apparatus according to a first embodiment.

Hereinafter, preferred embodiments of the present invention will be described in detail with reference to the drawings. In the drawings, the same reference numerals are used for identical or corresponding portions. Furthermore, in the drawings, the same reference numerals are appended to identical elements and redundant descriptions thereof will be omitted. Note also that the drawings are schematic diagrams for clearly illustrating the invention, and do not depict actual dimensions.

First Embodiment

Figure 2:
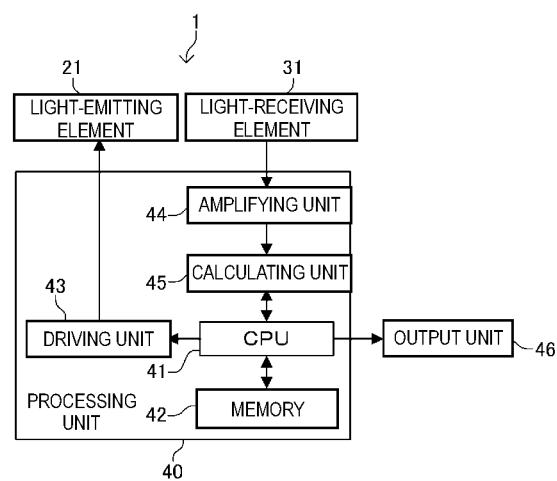
FIG. 2 is a block diagram illustrating the configuration of the biological information measurement apparatus according to the first embodiment.

First, the configuration of a biological information measurement apparatus 1 according to a first embodiment will be described with reference to FIGS. 1 and 2. FIG. 1 is a diagram illustrating the biological information measurement apparatus 1, where (*a*) is a top cross-sectional view, (*b*) is a side cross-sectional view, and (*c*) is a front cross-sectional view. In each of these diagrams, the contour of a finger F of a hand, which serves as a measurement area, is indicated by a broken line. In the following descriptions, a lengthwise direction of the finger F is defined as an x-axis direction, a direction perpendicular to the x-axis direction in the top view (see (*a*)) is defined as a y-axis direction, and a direction perpendicular to the x-axis direction in the side view (see (*b*)) is defined as a z-axis direction. In other words, assuming the finger F is viewed from the back of the hand in (*a*), the direction proceeding from the base to the tip of the finger F is defined as the x-axis direction, a width direction of the finger F is defined as the y-axis direction, and a height direction of the finger F is defined as the z-axis direction.

The biological information measurement apparatus 1 includes a substrate 10, a light-emitting unit 20, a light-receiving unit 30, a processing unit 40, and a main body 50. To simplify the drawings, the processing unit 40 is only illustrated in (*b*) of FIG. 1, and is not illustrated in (*a*) or (*c*). A biological sensor generally includes the substrate 10, the light-emitting unit 20, and the light-receiving unit 30. This biological sensor optically measures biological information such as a pulse, oxygen saturation, and the like using light absorption characteristics of bloodstream hemoglobin obtained through contact with a fingertip or the like. Although the present embodiment describes an example in which the biological information measurement apparatus 1 is attached to a finger, the present invention can also be applied in an apparatus attached to a toe, a forearm, an upper arm, or the like as long as the area to be measured has a lengthwise direction.

The substrate 10 is a thin, plate-shaped substrate formed in a rectangular shape of an insulative material (a dielectric) such as an insulative resin, a ceramic material, or the like. The substrate 10 is disposed such that a main surface 11 thereof is parallel to an x-y plane, with a long side of the substrate 10 being parallel to the x-axis and a short side being parallel to a y-axis. Recesses 12 and 13 are provided at diagonally opposite corner positions in the main surface 11 of the substrate 10 (on a diagonal line of the substrate 10, for example), and the light-emitting unit 20 and the light-receiving unit 30 are formed in the recesses 12 and 13, respectively.

The light-emitting unit 20 includes a light-emitting element 21 embedded in the recess 12, and the light-emitting element 21 is disposed so as to emit light through a sealing portion or the like (not shown) in the direction of the opening in the recess 12, or in other words, upward in the z-axis direction in (*b*) and (*c*) of FIG. 1. The light-emitting element 21 may be constituted of any element that emits light in the vicinity of infrared light having a high light absorption coefficient with respect to hemoglobin, such as an LED, a VCSEL (Vertical Cavity Surface Emitting LASER), a resonator-type LED, or the like.

The light-receiving unit 30 includes a light-receiving element 31 embedded in the recess 13 of the substrate 10, and the light-receiving element 31 is disposed so as to receive incoming light through a sealing portion or the like (not shown) from the direction of the opening in the recess 13, or in other words, from upward in the z-axis direction in (*b*) and (*c*) of FIG. 1. Accordingly, the light-receiving element 31 receives light emitted from the light-emitting element 21 and transmitted through a biological body (the finger F, in other words) or reflected by the finger F (detection light), photoelectrically converts the received detection light, and outputs a photoplethysmographic signal. A photodiode, a phototransistor, or the like is used as the light-receiving element 31.

According to the exemplary embodiment, the light-emitting element 21 and the light-receiving element 31 are light-shielded from each other by the substrate 10 due to the respective embedded configurations thereof. In other words, the configuration is such that the light-emitting unit 20 (the light-emitting element 21) is disposed on the main surface 11 side of the substrate 10 and irradiates the finger F, and the light-receiving unit 30 (the light-receiving element 31) is disposed on the main surface 11 side of the substrate 10 so as to be light-shielded from the light-emitting unit 20, and receives the light transmitted through or reflected by the finger F. Meanwhile, the position of the light-emitting unit 20 and the position of the light-receiving unit 30 may be switched. In other words, although the light-emitting unit 20 is disposed on the base side of the finger F and the light-receiving unit 30 is disposed on the tip side of the finger F in the present embodiment, the light-emitting unit 20 may be disposed on the tip side of the finger F and the light-receiving unit 30 may be disposed on the base side of the finger F. In addition, although the present embodiment is configured such that the long side of the substrate 10 is parallel to the lengthwise direction of the finger F (the x-axis direction), the configuration may be such that the short side of the substrate 10 is parallel to the lengthwise direction of the finger F (the x-axis direction). Furthermore, the light-emitting unit 20 and the light-receiving unit 30 may be formed in individual substrates that are isolated from each other.

As illustrated in (*a*) of FIG. 1, the light-emitting unit 20 and the light-receiving unit 30 are disposed such that when the substrate 10 is viewed in plan view, a line L that connects the light-emitting unit 20 and the light-receiving unit 30, or in other words, a line L that passes through the center of the light-emitting unit 20 and the center of the light-receiving unit 30 (called a "light emission-light receiving line L" hereinafter) is slanted relative to the lengthwise direction of the finger F (the x-axis direction). In other words, the light emission-light receiving line L intersects with the lengthwise direction of the finger F (the x-axis direction) at an angle greater than 0° and less than 90° in the x-y plan view. Note that the center of the light-emitting unit 20 and the center of the light-receiving unit 30 are defined as being substantially equivalent to the center of the light-emitting element 21 and the center of the light-receiving element 31, respectively.

The processing unit 40 will be described with reference to FIG. 2. FIG. 2 is a block diagram illustrating the configuration of the biological information measurement apparatus 1. The processing unit 40 includes a CPU 41, a memory 42, a driving unit 43, an amplifying unit 44, and a calculating unit 45, and an output unit 46 is connected thereto as necessary. The CPU 41 is a processor that controls the exchange of signals among the various units, and the memory 42 is a memory that stores programs and data. In other words, the CPU 41 realizes the functions of various units by executing programs stored in the memory 42.

The driving unit 43 drives the light-emitting element 21 (causes light to be emitted) in response to operating signals from the CPU 41. The amplifying unit 44 amplifies the photoplethysmographic signal obtained by the light-receiving element 31 photoelectrically converting the detection light. The calculating unit 45 obtains the biological information such as a pulse by processing the photoplethysmographic signal obtained from the amplifying unit 44. Note that the obtained biological information such as a pulse is stored in the memory 42 or outputted to the output unit 46. The output unit 46 may be constituted by a liquid-crystal display, a speaker, or the like, for example.

Returning to FIG. 1, the main body 50 includes a base portion 51 in which the substrate 10 is disposed and a cylindrical cover 52 (generally referred to as a guide) that covers the base portion 51, and a cylindrical hollow cavity portion H is formed by the main surface 11 of the substrate 10, the base portion 51, and the cover 52. Assuming a center axis C of the hollow cavity portion H resembles the axis of the finger F, the light-emitting unit 20 and the light-receiving unit 30 are disposed such that the light emission-light receiving line L is slanted relative to the center axis C of the hollow cavity portion H. To rephrase, the light emission-light receiving line L intersects with the center axis C of the hollow cavity portion H at an angle greater than 0° and less than 90°.

The cover 52 functions as a guide for holding the finger F in the hollow cavity portion H thereof and regulating a position where the finger F makes contact with the main surface 11 of the substrate 10. In other words, by inserting the finger F into the hollow cavity portion H, the finger F makes contact with and is placed upon the main surface 11 of the substrate 10. Note that the hollow cavity portion H is designed such that an inner diameter thereof is slightly greater than an outer diameter of a standard-size finger F. Accordingly, a subject can place his or her finger F in contact with the main surface 11 of the substrate 10 by inserting the finger F into the hollow cavity portion H, and the angle formed between the light emission-light receiving line L and the lengthwise direction of the finger can be slanted even in light of varying finger F sizes, varying insertion states, and so on.

Figure 3:
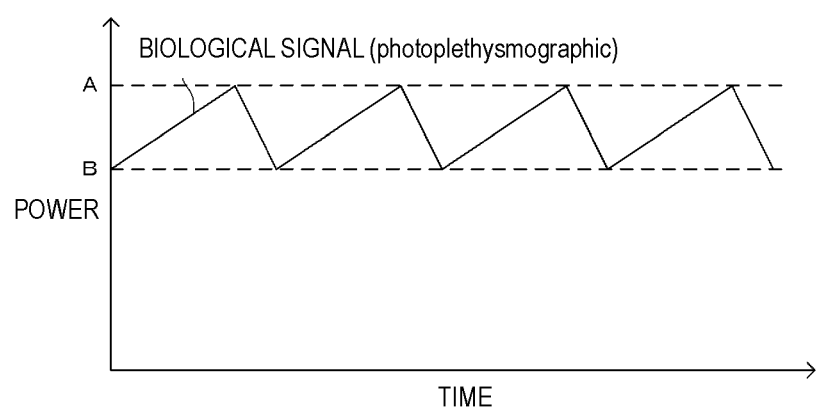
FIG. 3 is a diagram illustrating a definition of a SN ratio.

Next, the SN ratio according to the present embodiment will be defined using FIG. 3. In FIG. 3, the horizontal axis represents time and the vertical axis represents the strength (power) of the photoplethysmographic signal. As illustrated in FIG. 3, the photoplethysmographic signal has a power A, when hemoglobin absorbs the least amount of light, and a power B, when the hemoglobin absorbs the most amount of light, with the power A and the power B repeating periodically. Here, the power A is a value corresponding to the total of an AC component, which is a biological signal containing the biological information, and a DC component, which is stray light, and the power B is a value corresponding to stray light. As such, the SN ratio is expressed as (A–B)/B.

Here, SN ratios were calculated through simulations for the biological information measurement apparatus 1 according to the present embodiment, a biological information measurement apparatus 2A according to a first comparative example, and a biological information measurement apparatus 2B according to a second comparative example.

Figure 4:
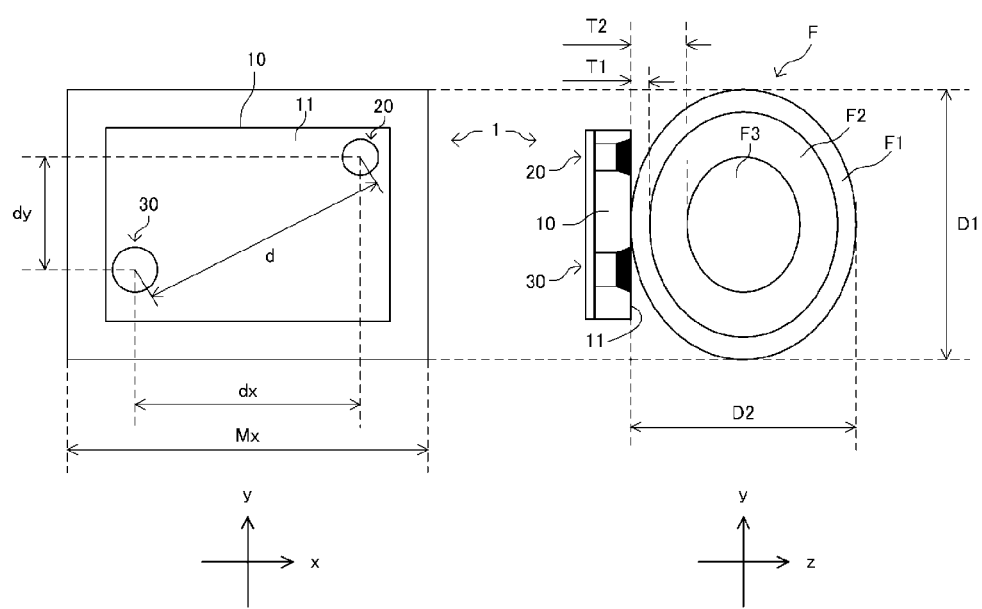
FIG. 4 is a diagram illustrating calculation conditions in a simulation for finding a SN ratio, performed by the biological information measurement apparatus according to the first embodiment.

Calculation conditions in the simulation according to the present embodiment will be described using FIG. 4. The left side of FIG. 4 illustrates a top view (an x-y plane) of the finger F and the substrate 10, whereas the right side illustrates a front cross-sectional view (a z-y plane). Referring to FIG. 4 (the left side), a distance d between the center of the light-emitting unit 20 and the center of the light-receiving unit 30 is 9.65 mm, a measurement range Mx in the x-axis direction is 10.9 mm, and the configuration is such that the substrate 10 is disposed in the center of the measurement range. A separation distance dx between the center of the light-emitting unit 20 and the center of the light-receiving unit 30 in the x-axis direction is 8.0 mm, and a separation distance dy in the y-axis direction is 5.4 mm. Accordingly, an angle of 34° is formed between the light emission-light receiving line L and the x-axis.

As illustrated in FIG. 4 (the right side), it is assumed that the finger F is constituted by an outermost skin layer F1, a blood layer F2 on the inner side thereof, and an innermost layer of bone F3. In the y-z plane cross-section of the finger F, the finger F has an outer diameter D1 of 15 mm in the y-axis (finger width) direction of the finger F and an outer diameter D2 of 12 mm in the z-axis (finger height) direction. A thickness T1 of the skin layer F1 is 1 mm, and a total thickness T2 of the skin layer F1 and the blood layer F2 is 2 mm.

Figure 5:
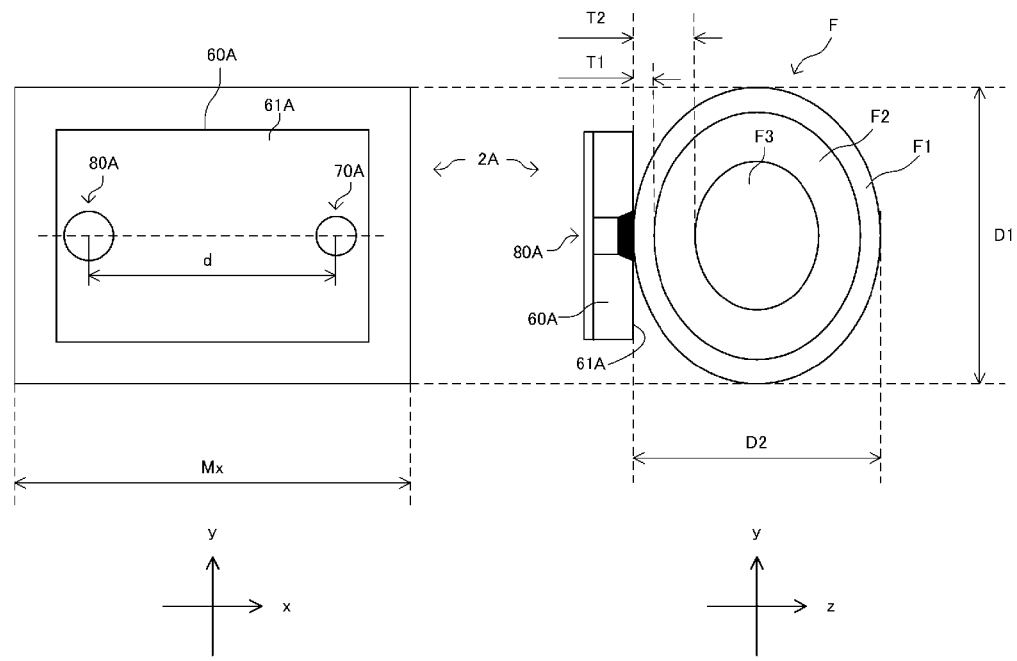
FIG. 5 is a diagram illustrating calculation conditions in a simulation for finding a SN ratio, performed by a biological information measurement apparatus according to a first comparative example.

Calculation conditions in the simulation according to the first comparative example will be described using FIG. 5. As illustrated in FIG. 5, the biological information measurement apparatus 2A according to the first comparative example is configured such that the light emission-light receiving line L between a light-emitting unit 70A and a light-receiving unit 80A formed in a main surface 61A of a substrate 60A is parallel to the x-axis (the lengthwise direction of the finger F). As illustrated in the left side of FIG. 5, the distance d between the center of the light-emitting unit 70A and the center of the light-receiving unit 80A is the same 9.65 mm as in FIG. 4, and the y-z cross-sectional structure of the finger F is also the same as that described in the first embodiment with reference to FIG. 4.

Figure 6:
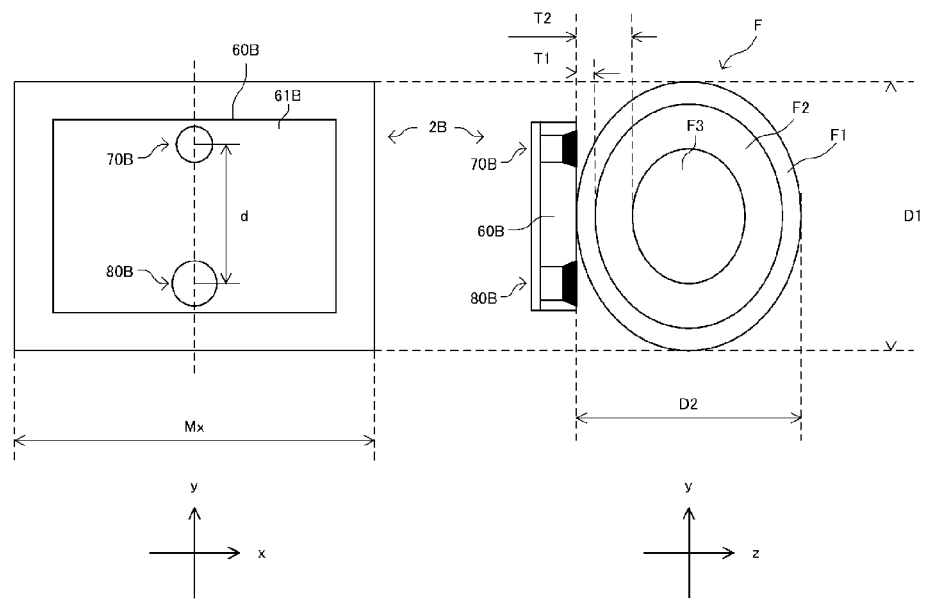
FIG. 6 is a diagram illustrating calculation conditions in a simulation for finding a SN ratio, performed by a biological information measurement apparatus according to a second comparative example.

Calculation conditions in the simulation according to the second comparative example will be described using FIG. 6. As illustrated in the left side of FIG. 6, the biological information measurement apparatus 2B according to the second comparative example is configured such that the light emission-light receiving line L between a light-emitting unit 70B and a light-receiving unit 80B formed in a main surface 61B of a substrate 60B is orthogonal to the x-axis (the lengthwise direction of the finger F). As illustrated in the left side of FIG. 6, the distance d between the center of the light-emitting unit 70B and the center of the light-receiving unit 80B is 9.65 mm, and the y-z cross-sectional structure of the finger F is also the same as that described in the first embodiment with reference to FIG. 4.

With respect to each of the coefficients for calculations, a refractive index of the skin layer is 1.4, a refractive index of the blood layer is 1.4, and a refractive index of the bone is 1.54. A skin absorption coefficient is 0.01 mm$^{-1}$, a skin scattering coefficient is 20 mm$^{-1}$, a hemoglobin absorption coefficient is 0.2 mm$^{-1}$, and a hemoglobin scattering coefficient is 20 mm$^{-1}$. In the scattering model, the Henyey-Greenstein function was set to g=0.9, the mean free path was set to 0.05, the scattering angle setting was 360°, and the input power was set to 1 W. These coefficients are the same in the first embodiment, the first comparative example, and the second comparative example.

Table 1 below illustrates the results of the stated simulations. With respect to the values A and B in the table, A represents a reception power of the photoplethysmographic signal when hemoglobin absorbs the least amount of light, and B represents the reception power of the photoplethysmographic signal when the hemoglobin absorbs the most amount of light, as described above with reference to FIG. 3.

TABLE 1

| | Light Reception Power (W) | | |
| --- | --- | --- | --- |
| | A (minimum light absorption) | B (maximum light absorption) | SN Ratio (A – B)/B |
| First Embodiment | 7.91E–6 | 4.55E–6 | 0.741 |
| First Comparative Example | 9.46E–6 | 5.87E–6 | 0.610 |
| Second Comparative Example | 3.45E–7 | 2.10E–7 | 0.639 |

As can be seen from Table 1, the SN ratios of the biological information measurement apparatus 2A according to the first comparative example and the biological information measurement apparatus 2B according to the second comparative example are 0.610 and 0.639, respectively, while the SN ratio of the biological information measurement apparatus 1 according to the present embodiment is 0.741, for a marked improvement.

To be more specific, while the amplitude of the AC component of the photoplethysmographic signal (A-B) is 3.59E-6 W in the first comparative example, that amplitude is 3.36E-6 W in the first embodiment, for a decrease rate of approximately 6% in the AC component in the first embodiment relative to the AC component in the first comparative example. On the other hand, while the DC component of the photoplethysmographic signal (B) is 5.87E-6 W in the first comparative example, the DC component is 4.55E-6 W in the first embodiment, for a decrease rate of approximately 22% in the DC component in the first embodiment relative to the DC component in the first comparative example. In this manner, the reduction of the DC component (22%) of the photoplethysmographic signal can be increased relative to the reduction rate of the AC component (6%) by slanting the light emission-light receiving line relative to the finger F, as in the first embodiment, from a state in which the light emission-light receiving line L is parallel to the finger F, as in the first comparative example. The result was an improvement of 21.5% from the SN ratio in the first comparative example (0.610) to the SN ratio in the first embodiment (0.741). To put this differently, in the case where the amplitude of the photoplethysmographic signal is the same in the first embodiment and the first comparative example, there is 21.5% less stray light in the first embodiment.

Meanwhile, while the amplitude of the AC component of the photoplethysmographic signal (A-B) is 1.35E-7 W in the second comparative example, that amplitude is 3.36E-6 W in the first embodiment, and thus the AC component in the first embodiment is approximately 25 times the AC component in the second comparative example. On the other hand, while the DC component of the photoplethysmographic signal (B) is 2.10E-7 W in the second comparative example, the DC component is 4.55E-6 W in the first embodiment, and thus the DC component in the first embodiment is approximately 22 times the DC component in the second comparative example. In this manner, the increase rate of the DC component (22 times) of the photoplethysmographic signal can be reduced relative to the increase rate of the AC component (25 times) by slanting the light emission-light receiving line relative to the finger F, as in the first embodiment, from a state in which the light emission-light receiving line L is perpendicular to the finger F, as in the second comparative example. The result was an improvement of 16.0%, from the SN ratio in the second comparative example (0.639) to the SN ratio in the first embodiment (0.741). To put this differently, in the case where the amplitude of the photoplethysmographic signal is the same in the first embodiment and the second comparative example, there is 16.0% less stray light in the first embodiment.

Figure 7:
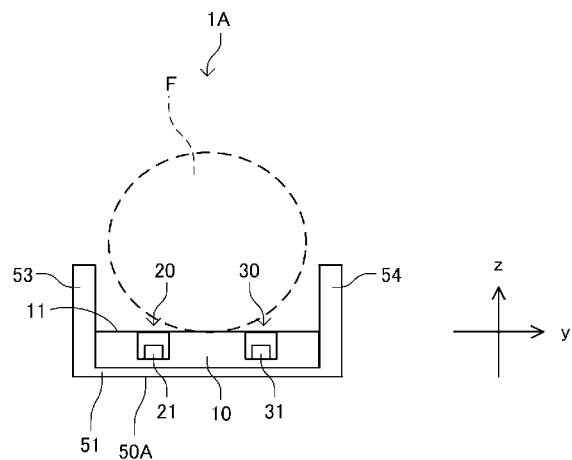
FIG. 7 is a diagram illustrating a variation on the biological information measurement apparatus according to the first embodiment.
Figure 8:
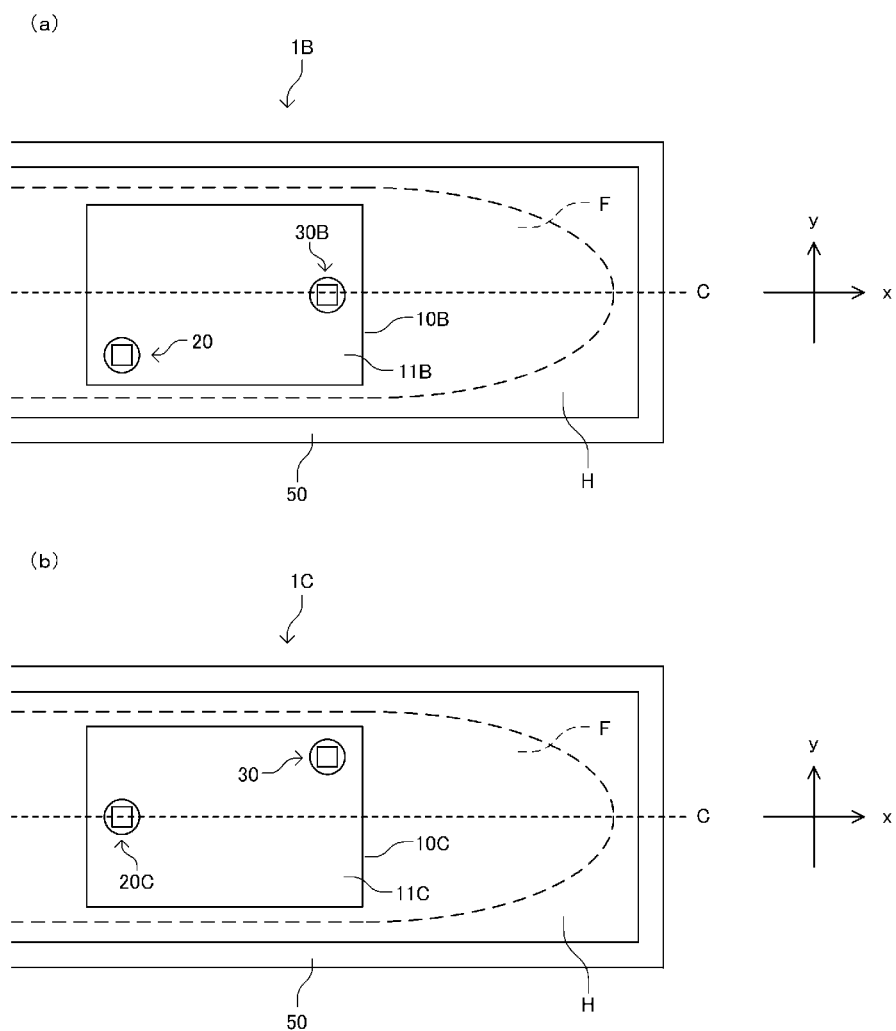
FIG. 8 is a diagram illustrating a variation on the biological information measurement apparatus according to the first embodiment.
Figure 9:
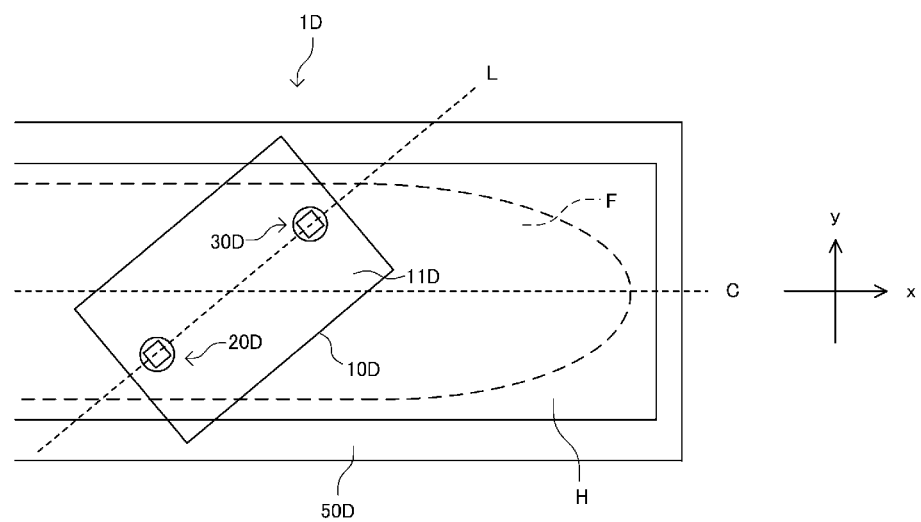
FIG. 9 is a diagram illustrating a variation on the biological information measurement apparatus according to the first embodiment.

FIGS. 7 to 9 illustrate various variations on the present embodiment. FIG. 7 illustrates a biological information measurement apparatus 1A serving as a variation on the first embodiment. Like (c) in FIG. 1, FIG. 7 illustrates a front cross-sectional view of the biological information measurement apparatus 1A, and the contour of the finger F, which serves as a measurement area, is indicated by a broken line.

The biological information measurement apparatus 1A includes the substrate 10, the light-emitting unit 20, the light-receiving unit 30, the processing unit 40 (not shown), and a main body 50A. Only the configuration of the main body is different from the biological information measurement apparatus 1 illustrated in FIG. 1. In the biological information measurement apparatus 1A, the main body 50A includes the base portion 51 and guides 53 and 54 (the guide) that are erected upright from the base portion 51 in the direction of the substrate 10 (the z-axis direction) and extend in the x-axis direction, and does not include a cover. Accordingly, a subject brings his or her finger F into contact with the main surface 11 of the substrate 10 with the finger F being guided or regulated by a space between the guides 53 and 54. In this manner, it is sufficient for the biological information measurement apparatus of the present invention to be configured such that when the subject brings his or her finger F into contact with the main surface 11 of the substrate 10, the light emission-light receiving line L is slanted relative to the lengthwise direction of the finger F when the substrate 10 is viewed in plan view. Accordingly, one of the guides 53 and 54 may be omitted as well, for example. In addition, as the guide, a line, a graphic, or the like may be provided on the main body 50A or the main surface 11 to indicate where the finger is to be placed, or a band for securing the finger F to the base portion 51 of the main body 50A may be provided in the base portion 51 or the guides 53 and 54.

Alternatively, the light-emitting unit and the light-receiving unit do not absolutely have to be in diagonally opposing corner positions of the substrate 10, as illustrated in the drawings of FIG. 8. (a) and (b) of FIG. 8 illustrate top cross-sectional views of biological information measurement apparatuses 1B and 1C respectively, which are variations on the first embodiment. The biological information measurement apparatuses 1B and 1C differ from the biological information measurement apparatus 1 illustrated in FIG. 1 only in terms of the x-y plane position of the light-emitting unit or the light-receiving unit in the substrate.

In the biological information measurement apparatus 1B illustrated in (a) of FIG. 8, the light-emitting unit 20 is disposed in a corner position of a substrate 10B in the same manner as the biological information measurement apparatus 1 illustrated in FIG. 1. However, a light-receiving unit 30B is disposed in a position centered in the y-axis direction (that is, on the center axis C) of the substrate 10B, in the same manner as the conventionally-configured substrate 60A illustrated in FIG. 5. Meanwhile, in the biological information measurement apparatus 1C illustrated in (b) of FIG. 8, the light-receiving unit 30 is disposed in a corner position of a substrate 10C in the same manner as the biological information measurement apparatus 1 illustrated in FIG. 1. However, a light-emitting unit 20C is disposed in a position centered in the y-axis direction (that is, on the center axis C) of the substrate 10C, in the same manner as the conventional substrate 60A illustrated in FIG. 5.

As such, when the substrate 10 is viewed in plan view, the light emission-light receiving line L is slanted relative to the lengthwise direction of the finger F in both the stated arrangement of the light-emitting unit 20 and the light-receiving unit 30B and the stated arrangement of the light-emitting unit 20C and the light-receiving unit 30. A configuration in which the position of one of the light-emitting unit and the light-receiving unit is offset from the center position in the y-axis direction, as in the present variation, makes it possible to form the other of the light-emitting unit and the light-receiving unit in the substrate using a conventional process. This in turn makes it possible to reduce changes to the process for manufacturing the conventionally-configured substrate 60A illustrated in FIG. 5, which keeps development costs down.

FIG. 9 illustrates a biological information measurement apparatus 1D serving as another variation on the present embodiment. The biological information measurement apparatus 1D includes a substrate 10D, a light-emitting unit 20D, a light-receiving unit 30D, the processing unit 40 (not shown), and a main body 50D. Note that the processing unit 40 has the same configuration and functions as that described in the first embodiment, and thus descriptions thereof will be omitted. Furthermore, the light-emitting unit 20D and the light-receiving unit 30D differ from the light-emitting unit 20 and the light-receiving unit 30 according to the first embodiment only in their respective locations on the substrate.

The substrate 10D is constituted by a rectangular substrate, with the light-emitting unit 20D and the light-receiving unit 30D disposed parallel to one pair of sides of the substrate 10D (the long sides, in the present embodiment), and the substrate 10D is disposed on the main body 50D such that the stated pair of sides is slanted relative to the x-axis direction. In the present embodiment, the light-emitting unit 20D and the light-receiving unit 30D are both disposed in the substrate 10D on a center line of the lengthwise direction of the substrate, in the same manner as the conventionally-configured substrate 60A illustrated in FIG. 5. Note that the light-emitting unit 20D and the light-receiving unit 30D do not necessarily have to be located on the substrate center line as long as those units are formed parallel to the sides of the substrate 10D. The light emission-light receiving line L, meanwhile, is slanted relative to the center axis C of the hollow cavity portion H. Such a configuration also makes it possible to dispose the light-emitting unit 20D and the light-receiving unit 30D such that the light emission-light receiving line L is slanted relative to the lengthwise direction of the finger F, which serves as the measurement area.

The main body 50D may have any configuration that defines the positional relationship between the substrate 10D and the finger F. In the main body 50D, the substrate 10D may be fixed, or the substrate 10D may be disposed so as to be movable relative to the main body 50D, such that the angle formed between the light emission-light receiving line L and the lengthwise direction of the finger F is variable. For example, the substrate 10D may be disposed so as to be rotatable in the x-y plane. In this case, the rotational center may be the center of the substrate 10D, or may be the position of the light-emitting unit 20D or the position of the light-receiving unit 30D.

According to the present variation, a configuration in which the light emission-light receiving line L is slanted relative to the lengthwise direction of the finger F can be realized using the substrate 10D having the same configuration as the conventionally-configured substrate 60A illustrated in FIG. 5. There is thus no need to change the process for forming the light-emitting unit 20D and the light-receiving unit 30D in the substrate 10D from the conventional process, which makes it possible to reduce development costs. Furthermore, a configuration that enables the angle formed between the light emission-light receiving line L and the lengthwise direction of the finger F to be varied makes it possible to specify or adjust the optimum angle of the substrate 10D relative to the finger F or the main body 50D for obtaining a desired SN ratio.

As described thus far, according to the present embodiment, the light-emitting unit 20 and the light-receiving unit 30 are disposed such that the light emission-light receiving line L is slanted relative to the lengthwise direction of the finger F, which serves as the measurement area. Through this, compared to the case where the light emission-light receiving line is parallel to the lengthwise direction of the finger, the DC component of the detection light, which acts as stray light, decreases by a greater ratio than the ratio in which the AC component of the detection light, which is necessary for obtaining the biological information, decreases, making it possible to greatly improve the SN ratio of the photoplethysmographic signal. Even compared to the case where the light emission-light receiving line is perpendicular to the lengthwise direction of the finger, the DC component of the detection light, which acts as stray light, increases by a smaller ratio than the ratio in which the AC component of the detection light, which is necessary for obtaining the biological information, increases, making it possible to greatly improve the SN ratio of the photoplethysmographic signal. Furthermore, according to the stated configuration, it is only necessary to change the positions of the light-emitting unit and the light-receiving unit in the substrate, or the positional relationship between the substrate and the main body, from the conventional biological information measurement apparatus, which makes it possible to avoid a substantial increase in manufacturing costs.

Second Embodiment

Figure 10:
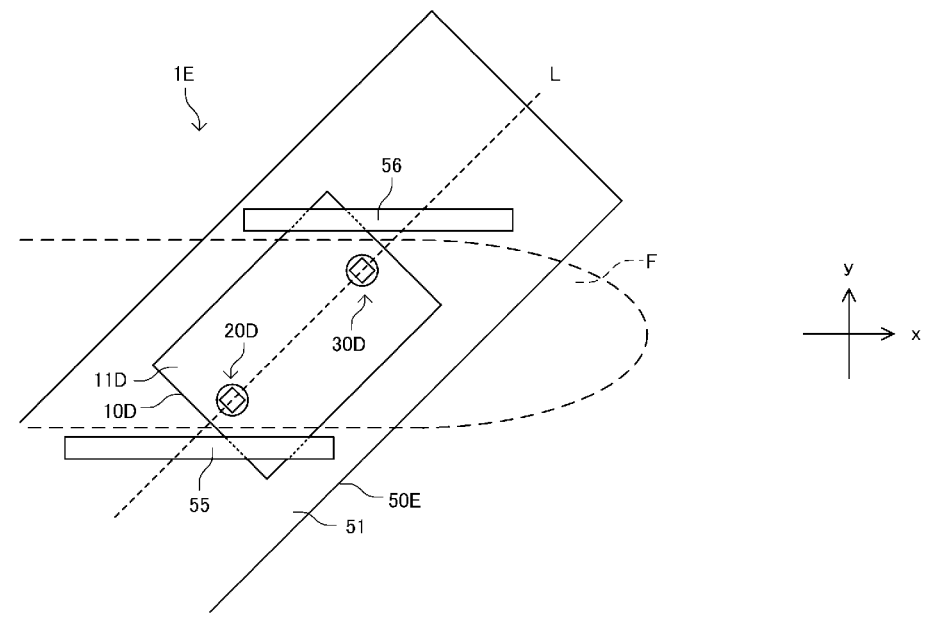
FIG. 10 is a diagram illustrating a biological information measurement apparatus according to a second embodiment.

The stated first embodiment describes a configuration in which the light emission-light receiving line L is slanted relative to the lengthwise direction of the finger F. The present embodiment, however, describes a configuration in which the lengthwise direction of the finger F is slanted relative to the light emission-light receiving line L. The configuration of a biological information measurement apparatus 1E according to the second embodiment will be described with reference to FIG. 10. FIG. 10 is a top cross-sectional view of the biological information measurement apparatus 1E, and the contour of the finger F of a hand, which serves as a measurement area, is indicated by a broken line.

The biological information measurement apparatus 1E includes the substrate 10D, the light-emitting unit 20D, the light-receiving unit 30D, the processing unit 40 (not shown), and a main body 50E. Note that the processing unit 40 has the same configuration and functions as that of the stated first embodiment, and the substrate 10D, the light-emitting unit 20D, and the light-receiving unit 30D have the same configurations and functions as those described in the variation on the first embodiment with reference to FIG. 9.

The main body 50E defines the position of the substrate 10 relative to the finger F, which serves as the measurement area. The main body 50E includes guides 55 and 56 serving as a guide for the finger f. The guides 55 and 56 are erected upright in the height direction of the finger, or in other words, upward in the z-axis direction, in the same manner as the guides 53 and 54 illustrated in FIG. 7, and extend in the lengthwise direction of the finger, or in other words, in the x-axis direction, as illustrated in FIG. 10. To rephrase, the guides 55 and 56 are disposed so as to be slanted relative to the lengthwise direction of the main body 50E or the direction in which the substrate 10 is disposed.

The biological information measurement apparatus 1E is configured such that when the finger F is placed between and regulated by the guide 55 and the guide 56, the light emission-light receiving line L is slanted relative to the direction in which the guides 55 and 56 extend or the lengthwise direction of the finger F (the x-axis direction). Note that the configuration may be such that one of the guides 55 and 56 is omitted. Furthermore, the guide is not limited to a guide as illustrated, and may be a cylindrical member through which the finger F is passed in the x-axis direction, a line, a graphic, or the like provided on the base portion 51 of the main body 50E to indicate where the finger is to be placed, or the like.

The biological information measurement apparatus 1E can enable a main surface 11D of the substrate 10D to contact the finger F from all directions. In other words, the main surface 11D can be brought into contact with the bottom of the finger F (the palm side), the back of the finger F, a side portion of the finger F, and the like.

According to the configuration of the present embodiment, the light-emitting unit 20D and the light-receiving unit 30D can be disposed such that the lengthwise direction of the finger F, which serves as the measurement area, is slanted relative to the light emission-light receiving line L, and thus the same effects as in the first embodiment, namely a great improvement in the SN ratio of the photoplethysmographic signal, can be achieved. Like the variation on the first embodiment illustrated in FIG. 9, a configuration in which the light emission-light receiving line L is slanted relative to the lengthwise direction of the finger F, which serves as the measurement area, can be realized in the present embodiment, using the substrate 10D configured in a conventional manner. The process for manufacturing the substrate 10D thus need not be changed from the conventional process, making it possible to reduce development costs.

REFERENCE SIGNS LIST 1, 1A, 1B, 1C, 1D, 1E BIOLOGICAL INFORMATION MEASUREMENT APPARATUS
10, 10B, 10C, 10D SUBSTRATE
20, 20C, 20D LIGHT-EMITTING UNIT
30, 30B, 30D LIGHT-RECEIVING UNIT
40 PROCESSING UNIT
50, 50A, 50D, 50E MAIN BODY
52 COVER (GUIDE)
53, 54, 55, 56 GUIDE (GUIDE)
F FINGER (MEASUREMENT AREA)
H HOLLOW CAVITY PORTION

The invention claimed is:

1. A biological information measurement apparatus comprising:
   a light emitter configured to emit light to irradiate a measurement area; and
   light receiver configured to receive light transmitted through or reflected by the measurement area and to photoelectrically convert the light to a photoplethysmographic signal comprising biological information, a substrate in which the light emitter and the light receiver are disposed; and
   a guide structurally configured to direct a position of the measurement area relative to the substrate,
   wherein, in a plan view, the light emitter and the light receiver are disposed in a plane perpendicular to at least one of a direction of the emitted light and a direction of the received light, and
   wherein the light emitter and the light receiver are positioned such that a line intersecting centers of each the light emitter and the light receiver is diagonal relative to a lengthwise direction of the measurement area, and
   wherein the substrate comprises a rectangular shape with the light emitter and the light receiver being disposed at diagonally opposing corner areas of the rectangular substrate, and one pair of sides of the substrate is parallel to a center axis of the guide.

2. The biological information measurement apparatus according to claim 1, further comprising a processing unit configured to obtain the biological information based on the photoplethysmographic signal.

3. The biological information measurement apparatus according to claim 1, further comprising:
   a substrate in which the light emitter and the light receiver are disposed; and
   a main body including a guide for directing a position of the measurement area relative to the substrate.

4. The biological information measurement apparatus according to claim 3,
   wherein the measurement area is a finger, and
   wherein the guide is a cover having a cylindrical hollow cavity structurally configured to receive the finger, such that the line intersecting the centers of the light emitter and the light receiver is diagonal relative to a center axis of the cylindrical hollow cavity.

5. The biological information measurement apparatus according to claim 3, wherein the guide comprises at least one guiderail that extends in a direction parallel to the lengthwise direction of the measurement area.

6. The biological information measurement apparatus according to claim 1, further comprising:
   a substrate in which the light emitter and the light receiver are disposed; and
   a main body configured to define a position of the substrate relative to the measurement area.

7. The biological information measurement apparatus according to claim 6,
   wherein the measurement area is a finger; and
   the substrate comprises a rectangular shape and the light emitter and the light receiver are disposed parallel to a pair of sides of the substrate, such that the pair of sides is diagonal relative to the lengthwise direction of the measurement area.

8. The biological information measurement apparatus according to claim 6, wherein the substrate is rotatable relative to the main body such that an angle between the lengthwise direction of the measurement area and the line intersecting the centers of the light emitter and the light receiver is variable.

9. The biological information measurement apparatus according to claim 1, further comprising a substrate in which the light emitter and the light receiver are disposed, wherein one of the light emitter and the light receiver is disposed on a center line bisecting the substrate and the other of the light emitter and the light receiver is offset from the center line of the substrate.

10. A biological information measurement apparatus comprising:
    a main body including a guide configured to position a finger of a person in a lengthwise direction of the main body;
    a planar substrate disposed in a base of the main body;
    a light emitter disposed in the planar substrate and configured to emit light to irradiate the finger; and
    a light receiver disposed in the planar substrate and configured to receive light transmitted through or reflected by the finger and to photoelectrically convert the received light to a photoplethysmographic signal comprising biological information of the person,
    wherein the light emitter and the light receiver are positioned such that a line intersecting centers of each the light emitter and the light receiver is diagonal relative to the lengthwise direction of main body, and
    wherein the planar substrate comprises a rectangular shape with the light emitter and the light receiver being are disposed at diagonally opposing corner areas of the rectangular planar substrate, and one pair of sides of the planar substrate is parallel to a center axis of the guide of the substrate is parallel to a center axis of the cylindrical hollow cavity.

11. The biological information measurement apparatus according to claim 10, further comprising a processing unit configured to obtain the biological information based on the photoplethysmographic signal.

12. The biological information measurement apparatus according to claim 10, wherein the guide is a cover having a cylindrical hollow cavity structurally configured to receive the finger, such that the line intersecting the centers of the light emitter and the light receiver is diagonal relative to a center axis of the cylindrical hollow cavity.

13. The biological information measurement apparatus according to claim 10, wherein the guide comprises at least one guiderail that extends the lengthwise direction.

14. The biological information measurement apparatus according to claim 10, wherein the guide comprises a pair of guiderails that extend in the lengthwise direction.

15. The biological information measurement apparatus according to claim 10, wherein the main body is configured to define a position of the substrate relative to the finger.

16. The biological information measurement apparatus according to claim 15, wherein the substrate comprises a rectangular shape and the light emitter and the light receiver are disposed parallel to a pair of sides of the substrate, such that the pair of sides of the substrate is diagonal relative to the lengthwise direction of the finger.

17. The biological information measurement apparatus according to claim 16, wherein the substrate is rotatable relative to the main body such that an angle between the lengthwise direction of the finger and the line intersecting the centers of the light emitter and the light receiver is variable.

18. The biological information measurement apparatus according to claim 10, wherein one of the light emitter and the light receiver is disposed on a center line bisecting the substrate and the other of the light emitter and the light receiver is offset from the center line of the substrate.

* * * * *